US010030232B2

(12) United States Patent
Dekker et al.

(10) Patent No.: US 10,030,232 B2
(45) Date of Patent: Jul. 24, 2018

(54) METHODS FOR PREPARING INACTIVATED ROTAVIRUS

(71) Applicant: Elanco Tiergesundheit AG, Indianapolis (IN)

(72) Inventors: Brent E. Dekker, Larchwood, IA (US); John M. Herbert, Larchwood, IA (US); Michael J. Reimnitz, Larchwood, IA (US)

(73) Assignee: Elanco Tiergesundheit AG, Greenfield, IN (US)

( * ) Notice: Subject to any disclaimer, the term of this patent is extended or adjusted under 35 U.S.C. 154(b) by 0 days.

(21) Appl. No.: 14/898,506

(22) PCT Filed: Jul. 18, 2014

(86) PCT No.: PCT/US2014/047164
§ 371 (c)(1),
(2) Date: Dec. 15, 2015

(87) PCT Pub. No.: WO2015/010002
PCT Pub. Date: Jan. 22, 2015

(65) Prior Publication Data

US 2016/0145583 A1 May 26, 2016

Related U.S. Application Data

(60) Provisional application No. 61/856,294, filed on Jul. 19, 2013.

(51) Int. Cl.
*A61K 39/15* (2006.01)
*A61K 39/00* (2006.01)
*A61K 39/12* (2006.01)
*C12N 7/00* (2006.01)
*A61K 39/39* (2006.01)

(52) U.S. Cl.
CPC ................ *C12N 7/00* (2013.01); *A61K 39/12* (2013.01); *A61K 39/15* (2013.01); *A61K 2039/5252* (2013.01); *A61K 2039/55566* (2013.01); *C12N 2720/12321* (2013.01); *C12N 2720/12332* (2013.01); *C12N 2720/12334* (2013.01); *C12N 2720/12361* (2013.01)

(58) Field of Classification Search
CPC .... A61K 39/12; A61K 2300/00; A61K 39/15; A61K 2039/5252; C12N 2720/12334
See application file for complete search history.

(56) References Cited

FOREIGN PATENT DOCUMENTS

| | | | |
|---|---|---|---|
| WO | WO 2008/039022 | A1 | 4/2008 |
| WO | WO2008039022 | * | 4/2008 |
| WO | WO 2009/032913 | A2 | 3/2009 |
| WO | WO2009032913 | * | 3/2009 |
| WO | 2012093406 | A2 | 7/2012 |

OTHER PUBLICATIONS

Song, H., Li, J., Shi, S., Yan, L., Zhuang, H., & Li, K. (2010). Thermal stability and inactivation of hepatitis C virus grown in cell culture. *Virology journal*, 7(1), 40.
Estes, Mary Kolb, et al. "Rotavirus stability and inactivation." Journal of General Virology 43(2) (1979): 403-409.
Bruce, M. G., et al. "Recognition of rotavirus antigens by mouse L3T4-positive T helper cells." Journal of General Virology 75(8) (1994): 1859-1866.
Jiang, Baoming, et al. "Immunogenicity of a thermally inactivated rotavirus vaccine in mice." Human Vaccines 4(2) (2008): 143-147.

* cited by examiner

*Primary Examiner* — Barry A Chestnut
(74) *Attorney, Agent, or Firm* — David L Pflugh

(57) ABSTRACT

Disclosed are methods for production of inactivated rotavirus directly from cell culture supernatants containing active or infectious rotavirus (e.g., bovine rotavirus), without prior isolation or purification of the rotavirus from the cell culture supernatants. In some embodiments, inactivated rotavirus (e.g., bovine rotavirus) is produced by heating a volume of culture supernatant to at least a temperature at which the rotavirus is inactivated. In some embodiments, the rotavirus (e.g., bovine rotavirus) is inactivated once the entire volume is heated to at least a temperature at which the rotavirus is inactivated. In some embodiments, the temperature of the cell culture supernatant is maintained for a suitable amount of time, which may be determined using any of the tests described herein. Inactivated rotavirus (e.g., bovine rotavirus) may then be isolated from the culture supernatant.

18 Claims, No Drawings

METHODS FOR PREPARING INACTIVATED ROTAVIRUS

The present application is a national phase entry under 35 U.S.C. § 371 of International Patent Application PCT/US2014/047164, filed on Jul. 18, 2014 and published in English as International Patent Publication WO2015/010002 A1 on Jan. 22, 2015, which claims benefit of priority to U.S. Pat. App. Ser. No. 61/856,294, filed Jul. 19, 2013; all of which are incorporated by reference in their entirety.

FIELD

This disclosure relates to the production of inactivated rotavirus directly from cell culture supernatant. Also disclosed are compositions containing inactivated rotavirus produced directly from cell culture supernatant.

BACKGROUND

One type of viral vaccine contains inactivated viruses. Active or infectious viruses can be inactivated so they no longer are infectious and can no longer replicate to produce progeny viruses. To be effective in a vaccine, however, inactivated viruses still must retain their ability to stimulate an immune reponse (i.e., retain immunogenicity) when administered to a subject.

Different methods exist for inactivating rotaviruses. In one method, rotavirus may be inactivated using chemicals. In one example, beta-propiolactone may be used as the chemical.

In another method for inactivating rotaviruses, heating the rotavirus (thermal inactivation) may be used. In known methods for heat inactivating rotaviruses, the viruses are isolated or purified from the environment in which they are typically found prior to thermal inactivation. In one example, rotavirus propagated on cultured cells is isolated from the cell culture medium or supernatant in which the virus unfected cells had been grown, prior to heat or thermal inactivation (PCT Publication No. WO2009/032913). In one example, the isolated rotaviruses are then suspended in an aqueous buffer having a specific osmolality (e.g., 200-500 mOsm), a specific concentration of a salt of a divalent cation (in the range of about 1 mM to 15 mM), and a specific amount of sugar and/or sugar alcohol (in the range of about 1 to 20% w/v) (PCT Publication No. WO2009/032913). The isolated rotaviruses, suspended in the aqueous buffer having the specific osmolality, divalent cation concentration and sugar/sugar alcohol concentration, is then thermally inactivated.

SUMMARY

Methods for producing inactivated rotaviruses from cell culture supernatants containing active or infectious rotaviruses by heating the cell culture supernatants are disclosed. In one example, the rotaviruses are bovine rotaviruses. In one example, the method for producing inactivated rotavirus comprises directly heating a volume of cell culture supernatant containing active rotavirus to a temperature at which the rotavirus is inactivated. Generally, rotavirus in the cell culture supernatant that has been directly heated is tested to ensure that the temperature and time for heating is suffucient and that active or infectious virus is no longer present. In one example, the cell culture supernatant does not have one or more of, an osmolality in the range of 200-500 mOsm, a concentration of a salt of a divalent cation in the range of about 1 mM to 15 mM, and a sugar and/or sugar alcohol in the range of about 1 to 20% weight/volume. The inactivated rotavirus is immunogenic. Generally, immunogenicity of the heat inactivated rotavirus is superior to immunogenicity of rotavirus inactivated chemically, for example, inactivated chemically with beta-propiolactone. In various examples, the cell culture supernatant may be filtered prior to heating. After thermal inactivation, the inactivated rotavirus may be isolated from the cell culture supernatant. Thermal inactivation of rotaviruses in cultured cell supernatant may be accomplished by heating at a temperature of at least about 60° C., or any of 65° C., 70° C., 75° C. or 80° C. These temperatures generally are maintained for a duration, after which, the rotaviruses are inactivated. In various examples, this may be for 15 minutes, 60 minutes, 120 minutes, 240 minutes, and other durations. Generally, substantially the entire volume of cell culture supernatant is heated to the temperature for the given time. In one example, the entire volume of cell culture supernatant is heated to the temperature for the given time. In one example, the method may also include a freezing step. Freezing of the cell culture supernatant may be carried out for at least about 12 hours, or for other durations. In some cases, cell culture supernatant that has been heated, then frozen, may be thawed and heated again, in one example, at the same temperature and for the same duration as the initial heating step. In one example, the pH of the cell culture supernatant is 7.6±0.1.

In another example, the method for producing inactivated rotavirus comprises collecting cell culture supernatant containing active rotavirus from cultured cells infected with rotavirus and directly heating a volume of the cell culture supernatant to a temperature at which the rotavirus is inactivated. In various examples, one or more additional steps may be included. For example, the cell culture supernatant may be filtered prior to directly heating, the cell culture supernatant may be frozen after it has been directly heated, and/or the rotavirus may be isolated from the cell culture supernatant after it has been directly heated. Generally, the rotavirus is tested after directly heating to ensure that active, infectious virus is not present.

Also disclosed are compositions comprising rotaviruses inactivated by the methods described herein. In addition to rotavirus inactivated by the disclosed methods, the compositions may also contain one or more adjuvants and/or pharmaceutically acceptable carriers. Various compositions may also contain antigens from one or more infectious agents in addition to rotavirus.

Also disclosed are methods for stimulating an immune response in a subject, comprising administering to the subject compositions containing rotaviruses inactivated by the methods described herein. In one example, the subject is a bovine animal. In one example, the composition is administered to the subject at least twice. The multiple administrations may be separated by various periods of time, between about two to twelve weeks, in one example. In the method, the compositions may be administered to the subject using a variety of routes, like subcutaneous, intravenous, intramuscular, intradermal, intranodal, intranasal, and oral.

Also disclosed are antibodies produced by administering the claimed compositions to a subject. The antibodies may be used in methods for neutralizing rotavirus by administering the antibodies to an animal.

DETAILED DESCRIPTION

Definitions

Herein, "rotavirus" means any of the rota viruses from the family Reoviridae. The rotaviruses may infect human or animal species (e.g., any of group A. B, C, D, E, F and/or G rotaviruses), including any strains, serotypes, genotypes, and/or reassortants thereof. In one example, the rotavirus infects bovine animals. Exemplary commercially available vaccines for human use that may be prepared using the methods described herein may include ROTARIX® (GlaxoSmithKline), ROTATEQ® (Merck Sharp & Dohme Corp.) and/or ROTOVAC (Bharat Biotech International). Exemplary commercially available vaccines for human use that may be prepared using the methods described herein may include Equine Rotavirus Vaccine (Pfizer), Calf Rotavirus Diarrhea Vaccine (Inactivate), ROTATEC® Corona (Merck Sharp & Dohme may also be used to prepare vaccines for use in non-human animals such as bovine, equine, and porcine individuals/populations.

Herein, “active rotavirus” or “live rotavirus” means rotaviruses that are infectious or able to multiply to produce progeny virus.

Herein, “inactive rotavirus” or “dead rotavirus” means rotaviruses that are not infectious or not able to multiply to produce progeny virus. Such viruses sometimes may be referred to as killed or inactivated. Herein, inactive rotaviruses are produced from active rotaviruses by heat treatment.

Herein, “cell culture supernatant” or “culture supernatant” means medium that has been used to support growth of cultured cells. Generally, herein, the cells have been infected with rotaviruses and the cell culture supernatant contains active progeny rotavirus produced by the infected cells.

Herein, “directly heating a volume of cell cell culture supernatant,” with respect to rotaviruses, generally refers to heating the cell culture supernatant to a temperature and for a time to produce complete inactivation of the rotavirus, without any prior isolation or purification of rotavirus from the cell culture supernatant. Therefore, no isolation or purification of rotavirus from the cell culture supernatant has occurred prior to thermal inactivation of virus in the cell culture supernatant.

Herein, “isolated rotavirus” means rotavirus that has been isolated or purified away from cell culture supernatant. In one example, rotavirus may be isolated away from cell culture supernatant by high-speed centrifugation (to pellet the virus) and then may be suspended in a aqueous buffer. The aqueous buffer containing the rotavirus may then be heated to thermally inactivate the rotavirus therein. The inventive methods described herein do not require isolation of rotavirus from the cell culture supernatant.

Rotaviruses Directly from Cell Culture Supernatant

Disclosed herein are methods for producing inactivated rotavirus by directly heating a volume of culture supernatant containing active rotavirus to a temperature at which the rotavirus is inactivated (e.g., thermal inactivation), and to compositions containing rotaviruses inactivated in this way. “Directly heating a volume of cell culture supernatant comprising live rotavirus” typically means that culture supernatant containing active (e.g., live, infectious, able to multiply to produce progeny virus) rotavirus is not treated or manipulated (e.g., no “pre-treatment”), other than being collected for processing, before the application of heat for inactivation of rotavirus. The virus is not isolated or purified from the culture supernatant prior to the heat treatment. Inactivated rotavirus generally refers to virus that is not active, not infectious and not able to multiply to produce progeny virus (e.g., is not productive). Inactivated rotavirus may be referred to as killed, dead and/or non-productive. Generally, at least for the purpose of being included in a vaccine, it is desirable that the inactivated rotavirus retain immunogenicity (e.g., the ability to stimulate an immune response) when administered to a subject. Generally, the methods described herein result in complete inactivation of active rotavirus contained within cell culture supernatant—no active rotavirus remains.

The inactivated rotavirus resulting from the disclosed methods is immunogenic, meaning that its administration to a subject will stimulate or produce an immune response in the subject. Generally, rotavirus inactivated using the methods described herein stimulates a better immune response in the subject compared to administration of an equivalent amount of rotavirus inactivated chemically, using beta-propiolactone in one instance (i.e., the thermally inactivated rotavirus is more immunogenic). Therefore immunogenicity of the thermally inactivated rotavirus is superior to immunogenicity of chemically inactivated rotavirus. Therefore, immunogenicity of thermally inactivated rotavirus may be superior to immunogenicity of chemically inactivated rotavirus, for example. Immune responses in a subject can be measured using a variety of methods known in the art.

In one example of directly heating a volume of cell supernatant (e.g., which may also be referred to as cultured cell supernatant) comprising rotavirus, the culture supernatant may be filtered (e.g., using a 70, 1.0 and/or 0.45 μm syringe filter or the like) prior to processing for inactivation (e.g., heating, etc.) but, in certain embodiments, this would not be considered pre-treatment of the culture supernatant. Filtering generally may remove cell debris, but does not isolate or purify the virus from the culture supernatant. Typically, however, if filtration is performed, it is after at least one heating step (e.g., as in Example 1). Prior art processes processes typically require some sort of isolation step, purification or virus concentration step, prior to inactivating the rotavirus. The methods described herein typically do not require an isolation step prior to inactivation. Thus, in the methods disclosed herein, the rotavirus does not need to be “isolated” (e.g., separated from the environment in which they are typically found, such as from the cultered cell supernatant) prior to heat inactivation.

In one example of the disclosed method, medium from cultured cells that have been infected with rotavirus is collected and, optionally, cell debris are removed (e.g., by filtration or low-speed centrifugation), but the rotavirus is not isolated or purified from the cell culture medium. The medium containing the rotavirus is then heat-treated to thermally inactivate the rotavirus.

In addition, the methods described herein do not require the rotavirus to be in any particular diluent buffer prior to inactivation. Generally, the rotavirus can be in any liquid environment in which the virus can remain active (e.g., conditions that do not inactivate the virus), prior to heat treatment. For example, the cell culture supernatant (or cultured cell supernatant) is not required to exhibit any particular osmolality, salt type and/or concentration (e.g., any particular type and/or amount of a salt of a divalent cation such as $CaCl_2$, $MgCl_2$ and/or $MgSO_4$), sugar or sugar alcohol (e.g., sorbitol, mannitol, glycerol, glucose, sucrose, lactose, maltose and/or trehalose) in order for the supernatant to serve as appropriate starting material (although one or more of these components may be present depending on the type of cell culture media being used). The methods described herein provide for the inactivation of rotavirus without first preparing the rotavirus in a diluent buffer having a pre-defined osmolality, salt and/or salt concentration, sugar or sugar alcohol therein (although, again, one or more of these components may be present depending on the type of cell culture media being used). For instance, a diluent buffer such as an aqueous buffer like a phosphate buffer, Tris buffer, citrate buffer, borate buffer, glycine buffer, acetate buffer, succinate buffer, HEPES buffer, maleate buffer, PIPES buffer, MOPS buffer, MOPSO buffer, histidine buffer, and/or $NaHCO_3$ buffer, with or without a particular pH (e.g., pH 5-9), is not required, but may be present, prior to heat inactivation. In addition, these methods do not require the presence or absence of any particular amino acids, vitamins, and/or the like, or any particular amounts thereof. In some embodiments, then, the methods described herein provide for directly heating a volume of any type of cell culture supernatant comprising live rotavirus (e.g., bovine rotavirus) without defining any particular osmolality, salt or salt concentration, sugar and/or sugar alcohol, buffer, amino acid and/or vitamin, pH being exhibited and/or present in the cell culture supernatant. Thus, in various embodiments, the rotavirus to be inactivated may be contained in or be present in any cell culture media suitable for culturing mammalian cells (e.g., especially those supporting the infection and production of rotavirus (e.g., bovine rotavirus) by such cells).

In one example of the disclosed method, the cultured cell supernatant containing the rotavirus to be thermally inactivated does not have one or more of an osmolality in the range of 200-500 mOsm, a concentration of a salt of a divalent cation in the range of about 1 mM to 15 mM), and a sugar and/or sugar alcohol in the range of about 1 to 20% w/v. Example salts of divalent cations may include, but are not limited to, $CaCl_2$, $MgCl_2$ and $MgSO_4$. Sugars may be monosaccharides or disaccharides. Example sugars and sugar alcohols may include, but are not limited to, sorbitol, mannitol, glycerol, glucose, sucrose, lactose, maltose and trehalose.

Thus, an advantage of the processes described herein is that the skilled artisan may simply obtain cell culture supernatant and begin processing the same without any initial pre-treatment and/or purification steps. Such steps may, of course, be performed after and/or in between heat inactivation steps to ultimately provide isolated, inactivated rotavirus and/or immunogenic antigens thereof.

Thermal Inactivation of Rotaviruses

Inactivation may be accomplished by obtaining cell culture supernatant comprising active rotavirus and heating the same to a temperature at which the rotavirus becomes inactive. A live, infectious and/or productively infectious rotavirus is typically one that is capable of infecting a cell and producing progeny therein. A non-infectious and/or not productively infectious rotavirus is a rotavirus that is not capable of infecting a cell and/or not capable of producing progeny therein. In some embodiments, the temperature to and/or at which the cell culture supernatant is heated is a temperature at which the rotavirus is inactivated (the "inactivation temperature", e.g., about 70° C. such as, for instance, 65° C., 67° C., 69° C., 70° C., 72.5° C., 75° C., 77.5° C., or 80° C.). The heating step typically takes place within a vessel (e.g., tube or flask). After heating, the cell culture supernatant may be transferred to a new vessel. In some embodiments, multiple heating steps are used. In such embodiments, the first heating step may be referred to as the initial heating step. The initial heating step may, optionally, be followed by a freezing step in which the cell culture supernatant is frozen at a suitable temperature (e.g., about −80° C.) for a suitable period of time (e.g., from one hour to overnight (e.g., eight hours) or more). The optional freezing step is typically performed in a new vessel. This freezing step may be then be followed by a second heating step, for example, using about the same conditions as the initial heating step (e.g., the inactivation temperature) to produce an inactivated rotavirus preparation. The inactivated rotavirus preparation may then be frozen until needed (e.g., for testing and/or use in a vaccine).

In some embodiments, the initial heating step may be the only heating step required to inactivate the rotavirus (e.g., the second heating step may not be necesssary). In such embodiments, the initial heating step may be carried out by raising the temperature of the entire volume of culture supernatant to the inactivation temperature and immediately carrying out the next step (e.g., freezing). Thus, in such embodiments, the cell culture supernatant is further processed (e.g., the next step(s) are carried out) as soon as the entire volume reaches the inactivation temperature. In other embodiments, the culture supernatant may be maintained at an inactivation temperature for a suitable amount of time (e.g., about any of 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, or 150 minutes) before further processing (e.g., carrying out the next step(s)). The second heating step may be carried out as described for the initial heating step (e.g., further processed as soon as the entire volume reaches the inactivation temperature or after the inactivation temperature is maintained for a suitable period of time). The freezing step typically separates the first and second heating steps. Freezing may also be used for storage of culture supernatant that has been heated such that rotavirus therein is inactivated.

In certain embodiments, the process may include raising the temperature of the cell culture supernatant to an appropriate temperature (e.g., about 70° C.) for an appropriate amount of time (e.g., about two hours), optionally subsequently freezing the cell culture supernatant after heating for a suitable period of time (e.g., about eight hours), and then optionally reheating the cell culture supernatant to an appropriate temperature (e.g., about 70° C.) for an appropriate amount of time (e.g., about two hours). The culture supernatant may then be filtered through an appropriate filter (e.g., a 10 or 70 μm filter).

Testing Heated Rotaviruses to Ensure Inactivation

Typically, preparations of rotavirus that have been treated to inactivate the virus, are tested to ensure that active virus is not present in the preparation (i.e., to ensure that the preparation contains only inactivated virus). The tests used generally will detect active virus (e.g., live, infectious, able to multiply to produce progeny virus). In one example of a test, preparations or a portion of preparations that have been treated to inactivate virus, are used to infect any cells permissive for infection by rotavirus. Presence of active virus in the preparation may be determined by, for example, fixing the cells and staining with a reagent for identifying rotavirus in the cells, as described above. Other methods of detecting active virus may be through the use of infectious center assays or assays to determine if progeny virus is produced by cells. A variety of methods may be used.

For example, the cells from which the cell culture supernatant may be obtained may include any cells permissive for infection by and replication of rotavirus (e.g., MA104, MDBK, VERO and other cells). The cells may be grown, for example, on plates, in roller bottles, in bioreactors, or using any means known in the art. To produce a suitable cell culture supernatant, cells may be cultured in the presence of an appropriate amount (e.g., MOI of 0.003) of live bovine rotavirus for an appropriate amount of time (e.g., two hours) under appropriate conditions (e.g., 37° C., 5% $CO_2$). Each sample may then be filtered (e.g., using a syringe filter (e.g., 1.0 μm)) and deposited into a new vessel. The sample may then be treated by, for example, heat as described herein, and optionally transferred to a new vessel. As samples are typically frozen after treatment, each may be thawed along with non-inactivated samples (e.g., positive control samples). The test samples may then be concentrated (e.g., 10×). Serial dilutions (e.g., ten-fold serial dilutions) of each test sample may then be prepared. Established test cells (three day culture, monolayer, 100% confluence (e.g., MA104 cells) may then be washed and the media replaced with an appropriate media (e.g., 0% DME (HyClone)). Test samples may then be added to each well/bioreactor (e.g., GE Hollow Fiber, RFP-50-C-3MA) containing test cells, followed by an appropriate incubation period (e.g., two hours at 37° C., 5% $CO_2$) to allow adsorption of rotavirus to the cells. The cells may then be washed and refed with media (e.g., DME (HyClone) containing 20 ml/L L-glutamine (ASL 31012) and 2 ml/L trypsin). After an appropriate amount of time (e.g., three days), the cells may be fixed (e.g., using 80% acetone) and stained with a reagent for identifying rotavirus (e.g, a bovine rotavirus monoclonal antibody followed by a detection reagent (e.g., a secondary antibody)) and analyzed for the presence of anti-rotavirus antibodies on the cells. Typically, rotavirus would not be detected in any negative control or samples in which rotavirus has been inactivated. In contrast, positive control samples and those in which rotavirus has not been inactivated would be stained positively.

Uses of Thermally Inactivated Rotavirus

The methods described herein may be used to produce vaccines for administration to a subject. As used herein, "a subject" or "a host" typically means an individual. A subject or host may include domesticated animals, such as cats and dogs, livestock (e.g., cattle, horses, pigs, sheep, and goats), laboratory animals (e.g., mice, rabbits, rats, guinea pigs) and birds. In some embodiments, the subject or host may be a mammal such as a primate or a human.

Thus, this disclosure also describes methods for stimulating an immune response specific for rotavirus in a subject and/or immunizing a subject against rotavirus by administering thereto a composition comprising a rotavirus inactivated as described herein. This disclosure also describes the inactivated rotaviruses and compositions containing the rotaviruses that are used in the administering. Such methods and compositions may include the combination of such inactivated rotaviruses (or preparation comprising inactivated rotavirus) with one or more pharmaceutically acceptable carriers to produce a formulation suitable for administration thereto. Exemplary, suitable pharmaceutical carriers and their formulations may be described in, for example, *Remington's: The Science and Practice of Pharmacy,* 21$^{st}$ *Edition*, David B. Troy, ed., Lippicott Williams & Wilkins (2005). An appropriate amount of a pharmaceutically-acceptable salt may be used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Pharmaceutical compositions may also include carriers, thickeners, diluents, buffers, preservatives, surface active agents, adjuvants, immunostimulants. It will be apparent to those persons skilled in the art that certain carriers may be more preferable depending upon, for instance, the route of administration and concentration of composition being administered.

Pharmaceutical compositions may also include one or more active ingredients such as antimicrobial agents, anti-inflammatory agents and anesthetics. In addition to inactivated rotavirus, the pharmaceutical compositions may include additional antigens from other agents. Such compositions, containing antigens from multiple agents, may be called combination vaccines.

Adjuvants may also be included to stimulate or enhance the immune response. Non-limiting examples of suitable classes of adjuvants include those of the gel-type (i.e., aluminum hydroxide/phosphate ("alum adjuvants")), calcium phosphate, microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPLA) of, for example, *E. coli, Salmonella minnesota, Salmonella typhimurium*, or *Shigella exseri*), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAP), saponins (QS-21), EMULSIGEN® (e.g., EMULSIGEN® D)), synthetic (muramyl peptide derivatives (murabutide, threony-MDP), nonionic block copolymers (L121), polyphosphazene (PCCP), synthetic polynucleotides (poly A:U, poly I:C), thalidomide derivatives (CC-4407/ACTIMID)), RH3-ligand, or polylactide glycolide (PLGA) microspheres, 3-de-0-acylated monophosphoryl lipid A (3D-MPL), among others. Fragments, homologs, derivatives, and fusions to any of these toxins are also suitable, provided that they retain adjuvant activity.

An immunological composition may be, for instance, a pharmaceutical composition and/or formulation that, upon administration to a host (e.g., an animal), induces or enhances an immune response directed against rotavirus antigen(s) (e.g., immunogen) contained within the composition (e.g., inactivated rotavirus). Such responses may include the generation of antibodies (e.g., through the stimulation of B cells) or a T cell-based response (e.g., a cytolytic response), as described above, which may be protective or neutralizing (e.g., or not). A protective or neutralizing immune response may be one that is detrimental to the rotavirus (or cells containing the same) and beneficial to the host (e.g., by reducing or preventing infection). As used herein, protective or neutralizing antibodies and/or cellular responses may be reactive with rotavirus prepared as described herein and/or a cell harboring the same. Those antibodies and/or cellular responses may reduce or inhibit the severity, time, and/or lethality of rotavirus infection when tested in animals. An immunological composition may be one that, upon administration to a host, results in a therapeutic (e.g., typically administered during an active infection) and/or protective (e.g., typically administered before or after an active infection) and/or neutralizing immune response. Such an immunological composition may also be considered a vaccine.

Thus, in some embodiments, methods for treating and/or preventing rotavirus infection are also provided. Methods for treating one or more disease conditions caused by or involving rotavirus in a mammalian host comprising administering to the mammal at least one or more effective doses of inactivated rotavirus prepared as described herein (e.g., and/or one or more compositions and/or formulations comprising the same) are also provided. Generally, administering the inactivated rotavirus to a subject stimulates an immune response specific for the rotavirus in the subject. The inactivated rotavirus may be administered in an appropriate dosage amount. The inactivated rotavirus may be administered once or more; where administration takes place more than once, each may be in the same or different doses.

In certain embodiments, the inactivated rotavirus and/or antigens thereof may be administered to the subject by any route and in a suitable dosage amount about one, two, three, four, five, six, seven, eight, nine, ten, or more times. Suitable routes of administration may include, for instance, subcutaneous, intravenous, intramuscular, intradermal, intranodal, intranasal, and/or oral. The doses may also be separated in time from one another by the same or different intervals. For instance, the doses may be separated by about any of 6, 12, 24, 36, 48, 60, 72, 84, or 96 hours, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the inactivated rotavirus may be administered alone or in conjunction with other agents (e.g., antibiotics, other vaccines, nutrients, etc.). Such other agents may be administered about simultaneously or at a different time and/or frequency. Other embodiments of such methods may also be appropriate as could be readily ascertained by one of ordinary skill in the art.

Also provided are methods for eliciting the production of antibodies, which may be protective and/or neutralizing, and/or may be reactive to inactivated rotavirus prepared as described herein. Compositions and methods for using such antibodies are also provided herein. Methods of preparing and utilizing various types of antibodies are well-known to those of skill in the art and would be suitable for use (see, for example, Harlow, et al. *Antibodies: A Laboratory Manual*, Cold Spring Harbor Laboratory, 1988; Harlow, et al. *Using Antibodies: A Laboratory Manual, Portable Protocol No.* 1, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., about $-20°$ C. or $-70°$ C.), in lyophilized form, or under normal refrigeration conditions (e.g., about $4°$ C.). When stored in liquid form, it is preferred that a suitable buffer such as Tris-buffered saline (TBS) or phosphate buffered saline (PBS) is utilized. Antibodies and their derivatives may be incorporated into compositions described herein for use in vitro or in vivo. In some embodiments, the antibody, antibodies and/or mixture of antibodies may be reactive with rotavirus and could be used to prevent and/or treat rotavirus infection (e.g., by passive immunization). Other methods for making and using antibodies (e.g., for detecting rotavirus) are available to one of skill in the art and may also be suitable for use as would be readily ascertained by one of ordinary skill in the art.

The usefulness (e.g., immunogenicity) of any of the materials described herein may be assayed by any of the variety of methods known to those of skill in the art, including those described herein (e.g., virus serum neutrilization assay using mammalian cells). Any one or more of the assays described herein, or any other one or more suitable assays, may be used to determine the suitability of any of the materials described herein for an intended purpose. It is to be understood that these methods are exemplary and non-limiting; other assays may also be suitable. In certain embodiments, it is preferred that a composition and/or formulation comprising a rotavirus inactivated as described herein exhibit immunogenic properties (e.g., inducing a detectable and/or neutralizing and/or protective immune response following administration to a host). The presence of neutralizing and/or protective immune response may be demonstrated by showing that infection by a rotavirus is affected (e.g., decreased) in individuals (e.g., human being or other animal) to whom the inactivated rotavirus has been administered as compared to subjects to whom the materials have not been administered. Suitable animal models that may be used to make such a determination may include, for example, the rabbits and/or cattle as described herein in the Examples. For instance, one or more test animals (e.g., rabbits, cattle, or similar model) may be administered (e.g., subcutaneously, intramuscularly, intradermally, intranasally) an inactivated rotavirus prepared as described herein and then, after a suitable amount of time (e.g., about 1, 2, 3, 4, 5, 6, 7, 8, 9, or 10 weeks), be assayed to identify the product of anti-rotavirus antibodies and/or immune cells (e.g., T cells) and/or be challenged by live rotavirus to determine whether the animals are protected from infection and/or if the severity of infection is decreased. The animal(s) may be monitored for immune function (e.g., T cell activity, antibody production) following administration and/or challenge using standard techniques (e.g., virus neutralization assay, ELISA). Sera may be analyzed for total antibody response or for expression of particular subtypes. Statistical analysis (e.g., Fisher's exact test, Wilcoxon test, Mann-Whitney test or other tests) may be performed on the resulting data. Thus, the inactivated rotavirus, and/or compositions and/or formulations comprising the same, prepared as described herein (e.g., immunogenic compositions) may be used to prevent and/or treat diseases caused by rotavirus.

This disclosure provides one or more methods for producing inactivated rotavirus by directly heating a volume of cell culture supernatant comprising live rotavirus to a temperature at which the rotavirus is inactivated. The cell culture supernant may include or exhibit, or lack, any particular buffer, osmolality, salt concentration, sugar, sugar alcohol, pH, amino acid, and/or vitamin. The cell culture supernatant does not need to exhibit a pre-defined buffer, osmolality, salt concentration, sugar, sugar alcohol, pH, amino acid, and/or vitamin in order to be suitable for use in the methods described herein. The cell culture supernatant typically comprises and/or is derived from a cell culture media that is permissive for producing live bovine rotavirus from mammlian cells. As explained above, "directly heating a volume of cell culture supernatant comprising live rotavirus" typically means that culture supernatant comprising active (e.g., live) rotavirus is not treated (e.g., no "pre-treatment"), other than being collected for processing, or at least in any way that may result in inactivation of the rotavirus, prior to the application of heat for inactivation of rotavirus. In some methods, the inactivated rotavirus is isolated from the cell culture supernant after inactivation. In some embodiments, substantially the entire volume (e.g., 70, 80, 90, 95, or 99%) of culture supernatant may be heated to the temperature and, in some, the entire volume of culture supernatant is heated to the temperature. In certain embodiments, the temperature is at least about 60° C. to about 80° C. (e.g., about any of 60° C., 61° C., 62° C., 63° C., 64° C., 65° C., 65° C., 67° C., 68° C., 69° C., 70° C., 71° C., 72° C., 73° C., 74° C., 75° C., 76° C., 77° C., 78° C., 79° C., or 80° C.). In some embodiments, the temperature of the culture supernatant (e.g., substantially the entire volume or the entire volume) is maintained for at least about 15 minutes to at least about any of one, two, three, four, five, six, seven, eight, nine, ten, eleven or twelve hours. Certain embodiments further comprise freezing the culture supernatant after heating, although this is optional. Certain embodiments further comprise subsequently heating the culture supernatant at least once more (e.g., after an initial heating and/or freezing step). The temperature of the initial and subsequent heatings may be about the same. In some embodiments, the pH of the culture supernatant is 7.6±0.1. This disclosure also provides compositions comprising rotavirus (e.g., bovine rotavirus) inactivated and/or rotavirus (e.g., bovine rotavirus) antigens prepared by any of the methods described herein. Also provided are methods for immunizing an animal with such composition(s). In some embodiments, the animal is bovine. In some embodiments, the composition may be administered to the animal at least twice and such administrations may be separated by time (e.g., about any of one, two, three, four, five, six, seven, eight, nine, ten, eleven and/or twelve weeks). The composition(s) may be administered to the animal via any suitable route such as subcutaneous, intravenous, intramuscular, intradermal, intranodal, intranasal, and/or oral. This disclosure also provides methods for producing antibodies, an antibody or antibodies produced by such methods (e.g., further comprising isolating the antibody or antibodies), and compositions comprising such antibodies. Methods for using such antibodies are also provided (e.g., methods for neutralizing rotavirus (e.g., bovine rotavirus) in vitro or in vivo (e.g., by administering such antibody or antibodies of to an animal (e.g., bovine).

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. For instance, in some embodiments, "about" or "approximately" a particular value may indicate a value of 99%, 95%, or 90% of that value. As an example, where the volume of culture supernatant is 1 L, "about" or "approximately" 1 L may equal 0.99, 0.95 or 0.9 L. As another example, where the temperature is 70° C.), "about" or "approximately" 70° C. may equal 69° C., 66° C., or 63° C. It is to be understood that these are merely examples.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

When the terms prevent, preventing, and prevention are used herein in connection with a given treatment for a given condition (e.g., preventing infection), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. A treatment can "prevent" infection by resulting in the patient's displaying only mild overt symptoms of the infection; it does not imply that there must have been no penetration of any cell by the infecting microorganism.

Similarly, reduce, reducing, and reduction as used herein in connection with the risk of infection with a given treatment (e.g., reducing the risk of a rotavirus infection) typically refers to a subject developing an infection more slowly or to a lesser degree as compared to a control or basal level of developing an infection in the absence of a treatment (e.g., administration or vaccination using polypeptides disclosed). A reduction in the risk of infection may result in the patient's displaying only mild overt symptoms of the infection or delayed symptoms of infection; it does not imply that there must have been no penetration of any cell by the infecting microorganism.

All references cited within this disclosure are hereby incorporated by reference in their entirety. Certain embodiments are further described in the following examples. These embodiments are provided as examples only and are not intended to limit the scope of the claims in any way.

EXAMPLES

Example 1: Heat Inactivation of Rotavirus

To prepare rotavirus, MA104 (Monkey Kidney Cells) were cultured in bioreactors using CYTODEX-3 microcarriers at 4.0 g/L. The bioreactors were planted with $1.5 \times 10^5$ cells/ml at a 15 L working volume. After three to seven days, or when the micro-carrier beads reached greater than 95% confluence, each bioreactor was prepared for infection by bovine rotavirus (BRV) at a multiplicity of infection (MOI) of 0.003 (determined by conducting a nuclei count). Before infecting cells, BRV was incubated at 37° C. for one to three hours in fresh DMEM media (14.85 L) including type IX trypsin (22.5 ml Type IX trypsin stock solution, also including L-glutamine and gentamycin/amphotericin B) to produce BRV media. Prior to the addition of BRV media to the bioreactor, the micro-carrier beads were allowed to settle for a minimum of five minutes and about 90% of the spent media was removed. Warmed, fresh media (12.5 L DMEM media including Type IX trypsin) was then pumped into the bioreactors. Two and a half liters (2.5 L) of BRV media was then added thereto. Once infection was complete (e.g., within 24 hours after P02 drifted above the 20% set point without recovery), agitation at about 75 rpm was performed for about 15 to 20 minutes prior to harvest.

Harvested virus was then used for heat inactivation studies. In these studies, the harvested material was heated to 70° C. and 10 ml samples were removed every 15 minutes over eight hours. After four hours, the heated material was transferred to another container to complete the second four hour incubation at 70° C. Each sample was filtered through a 1.0 µm syringe filter and deposited into a new vessel. Each filtered sample was then placed into a 70° C. circulating water bath for two hours (with shaking two times during the two hour period) and transferred to a new vessel (a 10 ml sterile vial). In these experiments, each sample was then placed into a −80° C. freezer overnight. The samples were then placed into a 70° C. circulating water bath for two hours (with shaking two times during the two hour period) and transferred to a new vessel. These samples were then stored in a −80° C. freezer until testing.

BRV was also chemically inactivated using beta-propiolactone (BPL). Approximately 500 ml of BRV-infected MA104 cell culture supernatant was prepared. In this method, two ml of BPL solution (10%) was added to 18 ml chilled sterile water for every one liter of rotavirus-containing cell culture supernatant to be inactivated. The mixture was then mixed at 4° C. for a maximum of 24 hours. The mixture was then stored at 4° C. (typically providing a total inactivation time of less than 52 hours). One to two ml was removed for testing to determine whether the rotavirus was inactivated using the same methods as used or the heat-inactivated samples.

To test the samples, each was thawed along with non-inactivated samples (e.g., positive control samples). Ten fold serial dilutions of each sample were then prepared. Established test MA104 cells (three day culture, monolayer, 100% confluence) were washed and the media replaced with DME (HyClone) containing no serum. One ml of each test sample was then added to each well containing test cells, followed by a two hour incubation period (37° C., 5% $CO_2$) to allow adsorption. Two ml of refeed media DME containing no serum and containing 20 ml/L L-glutamine (ASL 31012) and 2 ml/L trypsin) was then added. After three days culture, the cells were fixed using 80% acetone and stained with a monoclonal antibody specific for BRV (82×100 NAH diluted 1:1000 in PBS for two hours at 37° C., stained with FITC Goat Anti-Mouse #55493 diluted in 1:1000 in PBS for two hours at 37° C.) and analyzed by detecting fluorescence. Rotavirus was not detected in any of the negative control wells and only rarely detected in wells containing dilutions of the heat-inactivated samples. Positive control sample wells were all positive for rotavirus. Only completely inactivated virus was used in further experiments.

In another test, one to two day cultures of MA104 cells (≥70% confluence) were prepared as described for the previous test (e.g., culture media removed and replaced with DME containing no serum. Rotavirus test samples were prepared by heating culture supernatant containing live rotavirus to 70° C. for one or two hours, followed by freezing at −80° C. until testing for inactivation (e.g., a single-step inactivation process). Other rotavirus test samples were prepared by heating culture supernatant containing live rotavirus to 70° C. for one or two hours, followed by freezing at −80° C., followed by a second heat inactivation step at 70° C. for one or two hours, and freezing at −80° C. until testing for inactivation (e.g., two-step inactivation process). The test MA104 cells were then incubated with the various rotavirus test samples for a minimum of three days and observed for cyotpathic effect (CPE). CPE was not observed in any of the negative control or heat-inactivated samples (one hour, two hour, single- or two-step inactivation process) indicating that each process completely inactivated the rotavirus present in the cell culture media. In contrast, CPE was observed in all positive control samples.

Example 2: Immunogenicity of Heat Inactivated Rotavirus

A. Rabbit Studies

This study compared the serological response of rabbits (not previously exposed to bovine rotavirus antigens (BR)) immunized with BR prepared using conventional beta-propiolactone (BPL-BR) inactivation protocol or the heat inactivation procedures described in Example 1 (termed "HI-BR"). Six Emulsigen adjuvanted vaccines (30% Emulsigen D) were tested. Before administering antigens, rabbits were bled to obtain a baseline geometric mean titer (GMT). Rabbits received a 1.25 ml subcutaneous priming dose on day 0(±2) and a subcutaneous boost dose on day 20(±2). Treatment groups were organized as shown in Table 1:

TABLE 1

| Group | Antigen | Number of rabbits |
|-------|---------|-------------------|
| 1 | 3X HI-BR* | 10 |
| 2 | 1X HI-BR | 10 |
| 3 | 0.5X HI-BR | 10 |
| 4 | 3X BPL-BR | 10 |
| 5 | 1X BPL-BR | 10 |
| 6 | 0.5X BPL-BR | 10 |

*X = standard BRV dose in commercial product.

Test serum was obtained at day 35 (e.g., approximately 14 days post vaccination (DPV)). GMT of the day 35 serum was assayed for anti-rotavirus antibody content using a virus neutralization assay (VNA) and ELISA. The VNA was carried out by heat inactivating test serum samples in a 56-58° C. waterbath for 30-60 minutes. MA104 cells (four to six day monolayers) were contacted with serial dilutions of test serum in dilution media (DMEM, 2% L-glutamine, 5% FBS, 0.2 ml/L gentamycin, 0.2 ml/L amphotericin B). Stock rotavirus was prepared in virus dilution media (DMEM, 2% L-glutamine, 700 ml/L Type IX trypsin, 0.2 ml/L gentamycin, 0.2 ml/L amphotericin B) to contain 50-500 $FAID_{50}$/ml of virus ($FAID_{50}$/ml=50% fluorescent antibody infectious dose per ml) and mixed for 45-60 minutes at room temperature. This virus solution was then serially diluted to 1:20,000-25,000 in dilution media, and the serial dilutions incubated with serum samples for 50-70 minutes. The virus-serum mixture (along with positive and negative controls) was then applied to the MA104 cells and the cells cultured for two to three days at 37° C. (5% $CO_2$ incubator). Cells were then washed, fixed using 80% acetone (30±5 minutes), and incubated with an anti-BRV primary antibody followed by a secondary fluorescent antibody. Titers were calculated using the Spearman-Karber method and reported as the reciprocal of the dilution of serum that inhibits viral growth in more than 50% of the indicator wells of the given dilution. ELISA was carried out using standard procedures. The results of these studies are summarized in Table 2:

TABLE 2

| Group | Average GMT (day 0) | Average GMT VNA (day 35/+14DPV2 (=day 14)) | Range GMT VNA (day 35/+14DPV2 (=day 14)) | Average ELISA (day 35/+14DPV2 (=day 14)) | Range ELISA (day 35/+14DPV2 (=day 14)) |
|---|---|---|---|---|---|
| 1 (3X HI-BR) | 2 | 3520 | 1218-19484 | 609 | 512-1024 |
| 2 (1X HI-BR) | 2 | 3189 | 1218-5793 | 323 | 128-1024 |
| 3 (0.5X HI-BR) | 2 | 4240 | 1722-8192 | 416 | 256-512 |
| 4 (3X BPL-BR) | 2 | 11 | 3-64 | 2 | 2 |
| 5 (1X BPL-BR) | 2 | 9 | 6-45 | 2 | 2-4 |
| 6 (0.5X BPL-BR) | 2 | 5 | 3-10 | 3 | 2-32 |

As shown in Table 2, heat-inactivated BR provided a much stronger antibody response, as measured by a virus-neutralization assay or ELISA, than BPL-inactivated BR.

B. Bovine Studies

This study compared the serological responses of bovine animals (the natural BRV host) that had not been previously vaccinated against rotavirus, to administration of bovine rotavirus antigens (BR) prepared using conventional beta-propiolactone (BPL-BR) inactivation protocol or the heat inactivation procedures described in Example I (HI-BR). Six EMULSIGEN adjuvanted vaccines (30% EMULSIGEN D) were tested (Table 3). Animals received a 5 ml intramuscular (IM priming dose (in the neck) on day 0 and a boosting dose (also IM) on study day 84 (I2 weeks post-immunization). Antibody levels were determined from serum samples obtained at study day(s) 0 (pre-bleed; animals typically have some anti-BRV antibodies due to colostral passive transfer), 14, 28, 56, 84, 98 and 112. Once collected, serum was stored at −20° C. Virus neutralization assays were performed essentially as described above except that the virus solution was serially diluted 1:2 and then to $10^{-1}$, $10^{-2}$, $10^{-3}$, $10^{-4}$ and $10^{-5}$ in dilution media.

Treatment groups were organized as shown in Table 3:

TABLE 3

| Group | Antigen | Number of animals |
|---|---|---|
| 1 | 3X HI-BR* | 10-15 |
| 2 | 1X HI-BR | 10-15 |
| 3 | 0.5X HI-BR | 10-15 |
| 4 | 3X BPL-BR | 10-15 |

*X = standard BR dose in commercial product

The results of this study are shown in Table 4:

TABLE 4

| Group | Average GMT (day 0) | Range GMT (day 0) | Average GMT VNA (day 98/+14DPV2 (=day 112)) | Range GMT VNA (day 98/+14DPV2 (=day 112)) |
|---|---|---|---|---|
| 1 (3X HI-BR) | 225 | 32-1448 | 9255 | 2263-30444 |
| 2 (1X HI-BR) | 175 | 45-861 | 11536 | 3805-25600 |
| 3 (0.5X HI-BR) | 193 | 91-1448 | 6321 | 1131-18102 |
| 4 (3X BPL-BR) | 186 | 91-1448 | 162 | 71-566 |

As shown in Table 4, heat-inactivated BR provided a much stronger antibody response as measured by a virus-neutralization assay than BPL-inactivated BR.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method for producing inactivated rotavirus, comprising directly heating a volume of cell culture supernatant containing active unmanipulated rotavirus to a temperature at which the rotavirus is inactivated;
   wherein the temperature is about 60-80° C.

2. The method of claim 1, wherein the cell culture supernatant does not have one or more of:
   an osmolality in the range of 200-500 mOsm,
   a concentration of a salt of a divalent cation in the range of about 1 mM to 15 mM, and
   a sugar and/or sugar alcohol in the range of about 1 to 20% weight/volume.

3. The method of claim 1, wherein the inactivated rotavirus is immunogenic.

4. The method of claim 3, wherein the inactivated rotavirus elicits a higher geometric mean titer of virus neutralizing antibodies than a rotavirus inactivated chemically.

5. The method of claim 1, wherein the rotavirus is a bovine rotavirus.

6. The method of claim 1, wherein the temperature is about 70° C.

7. The method of claim 1, wherein the temperature of the culture supernatant is maintained for about 15 minutes to about 240 minutes.

8. The method of claim 1, wherein the temperature of the culture supernatant is maintained for about 15 minutes to about 60 minutes.

9. The method of claim 1, wherein the temperature of the culture supernatant is maintained for about 60 minutes.

10. The method of claim 1, further comprising subsequently heating the cell culture supernatant in at least two separate steps.

11. The method of claim 1, wherein the pH of the cell culture supernatant is 7.6±0.1.

12. A composition comprising rotavirus inactivated by directly heating a volume of cell culture supernatant containing active unmanipulated rotavirus to a temperature at which the rotavirus is inactivated;
   wherein the temperature is about 60-80° C.; and
   wherein the temperature is maintained for about 15 to 240 minutes.

13. The composition of claim 12, further comprising an adjuvant.

14. The composition of claim 12, further comprising one or more pharmaceutically acceptable carriers.

15. The composition of claim 12, further comprising at least one antigen from an infectious agent other than rotavirus.

16. A method for stimulating an immune response in a subject, comprising administering to the subject the composition of claim 12.

17. The method of claim 16, wherein the subject is a bovine animal.

18. The method of claim 16, wherein the composition is administered to the subject via a route selected from the group consisting of subcutaneous, intravenous, intramuscular, intradermal, intranodal, intranasal, and oral.

* * * * *